(12) United States Patent
Ogawa et al.

(10) Patent No.: US 9,211,397 B2
(45) Date of Patent: Dec. 15, 2015

(54) PATCH FOR TREATMENT OF EYELID DISEASE CONTAINING CLOBETASOL

(71) Applicant: Senju USA, Inc., Woodland Hills, CA (US)

(72) Inventors: Takahiro Ogawa, Woodland Hills, CA (US); Akiharu Isowaki, Woodland Hills, CA (US); Koji Kawahara, Tokyo (JP); Takao Hiraoka, Tokyo (JP); Mariko Tanaka, Tokyo (JP); Chihiro Kenmochi, Tokyo (JP)

(73) Assignee: SENJU USA, INC., Woodland Hills, CA (US)

( * ) Notice: Subject to any disclaimer, the term of this patent is extended or adjusted under 35 U.S.C. 154(b) by 75 days.

(21) Appl. No.: 13/719,406

(22) Filed: Dec. 19, 2012

(65) Prior Publication Data
US 2014/0171886 A1 Jun. 19, 2014

(51) Int. Cl.
| | | |
|---|---|---|
| *A61L 15/58* | (2006.01) | |
| *A61K 9/70* | (2006.01) | |
| *C08L 67/04* | (2006.01) | |
| *A61L 15/24* | (2006.01) | |
| *C08L 23/06* | (2006.01) | |
| *A61L 15/26* | (2006.01) | |
| *A61L 15/44* | (2006.01) | |
| *A61M 35/00* | (2006.01) | |

(52) U.S. Cl.
CPC ............ *A61M 35/00* (2013.01); *A61K 9/7053* (2013.01); *A61K 9/7076* (2013.01); *A61L 15/24* (2013.01); *A61L 15/26* (2013.01); *A61L 15/44* (2013.01); *A61L 15/58* (2013.01)

(58) Field of Classification Search
None
See application file for complete search history.

(56) References Cited

U.S. PATENT DOCUMENTS

| | | | |
|---|---|---|---|
| 5,000,956 A | 3/1991 | Amkraut et al. | |
| 5,891,920 A * | 4/1999 | Hirano et al. | ............... 514/629 |
| 2006/0036220 A1 | 2/2006 | Kawahara et al. | |
| 2009/0022778 A1 | 1/2009 | Yamaji et al. | |

FOREIGN PATENT DOCUMENTS

| | | |
|---|---|---|
| JP | S63-230635 A | 9/1988 |
| JP | H05-17346 A | 1/1993 |
| WO | 2004/064817 A1 | 8/2004 |
| WO | 2006/092829 A1 | 9/2006 |

OTHER PUBLICATIONS

Young's Modulus (Tensile Modulas), [retrieved from on-line website: http://www.engineeringtoolbox.com/young-modulus-d_417.html, last visit Jul. 15, 2015].*

* cited by examiner

*Primary Examiner* — Ernst V Arnold
*Assistant Examiner* — Kyung Sook Chang
(74) *Attorney, Agent, or Firm* — Porter, Wright, Morris & Arthur LLP; Holly Kozlowski

(57) ABSTRACT

A patch for treatment of eyelid diseases that is provided with a support, a pressure-sensitive adhesive layer, and a release layer in this order, wherein (a) the pressure-sensitive adhesive layer includes the following (a-1) to (a-4): (a-1) a styrene-isoprene-styrene block copolymer, a tackifier resin, and a softening agent are contained; (a-2) a ratio (mass ratio) of the styrene-isoprene-styrene block copolymer and the tackifier resin is 1:2 to 1:4; (a-3) a content of the softening agent is 40% to 60% by mass; and (a-4) further 0.005% to 5% by mass of clobetasol or acid ester thereof is contained; and (b) the support has elastic modulus with a Young's modulus of 0.01 to 0.5 GPa: and a method for producing the patch for treatment of eyelid diseases including: forming a pressure-sensitive adhesive layer on a upper surface of a release layer.

13 Claims, No Drawings

PATCH FOR TREATMENT OF EYELID DISEASE CONTAINING CLOBETASOL

TECHNICAL FIELD

The present invention relates to a patch for treatment of eyelid diseases containing clobetasol or the acid ester thereof.

BACKGROUND ART

A patch used by applying onto the skin has a layer structure including a support, and a pressure-sensitive adhesive layer provided on at least one surface of the support. Further, in order to protect the front surface of the pressure-sensitive adhesive layer, a release layer is arranged, or for example, when the support is extremely thin and the like, a layer structure in which a carrier layer of a carrier film or the like is provided on the support may often be provided.

A patch is applied on the skin and then removed, thereafter in many cases, a new patch is applied, and thus the patch that does not fall off from the skin for an intended period of time, can be removed easily and beautifully, and further does not strongly stimulate the skin is required. In addition, when the patch is applied on an exposed area of the skin in daily life, it may be demanded that the applied site is unnoticeable.

In other words, it is required that a patch have an appropriate adhesive force. When the adhesive force is too weak, the patch may be easily removed from the surface of the skin, or the patch may not be applied along a skin surface with fine irregularities such as sulcus cutis. When the adhesive force is too strong, the patch may cause skin irritation, or the peeling off after use may become difficult.

A facial surface is an area where sebum is secreted largely as compared with an arm, a shoulder, and the like. When a patch is applied on a facial surface where sebum is secreted largely, particularly when a patch is applied on an eyelid, a pressure-sensitive adhesive of a pressure-sensitive adhesive layer absorbs the sebum that has been secreted from the skin of eyelid, and thus the cohesive force of the pressure-sensitive adhesive is decreased, and there may be a possibility that the patch is easily removed. Therefore, in order that the patch is not removed from the skin even when absorbing a large amount of sebum, it has been considered that the thickness of the pressure-sensitive adhesive layer is needed to be sufficiently thick.

In the facial surface, eyelid is a facial surface area that not only particularly draws the attention of other people but also has extremely large number of times of expansion and contraction by movements, such as a blinking that is repeated at all times. Therefore, for a patch applied on an eyelid, the eyelid is an area where not only the tackiness but also the less skin stimulation is strongly required.

By the way, chalazion, blepharitis, meibomian gland dysfunction, allergic conjunctivitis, vernal conjunctivitis, atopic conjunctivitis, and the like are known as diseases that are caused by inflammation of eyelid and palpebral conjunctiva. For example, chalazion is a mass of a meibomian gland that located on the back of eyelid in eyelid tissue, and as a method of the treatment, in addition to incision and scraping, a steroid therapy can be performed.

As a steroid therapy, an intralesional steroid injection has been performed. However, in the steroid injection, there is a pain at the time of injection, a formation of white subcutaneous (steroid) deposit at the injection site, and a complication after the steroid injection such as decoloration and atrophoderma, and in extremely rare cases, retina and choroid vascular occlusions may be caused after the steroid injection. Therefore, a removal treatment by surgical operation may be performed for the complete cure, however, imposes a heavy burden on the patient.

Therefore, in order to resolve these problems, a patch containing steroid for treatment of eyelid disease is desired. From Patent Literature 1 (WO 2004/064817), a patch in which a remedy for eyelid diseases such as adrenal cortical hormone is mixed has been known. A patch for treatment of eyelid diseases is less transferred into the eyes (tear fluid) as compared with other ophthalmic drop formulations such as eyedrops, and has the advantage that a risk of ocular hypertension or cataract induced by steroid can be reduced. Further, in the patch, pain by an injection or surgical operation is not accompanied, the sustainability of the drug is kept, and a short-term treatment is expected.

An eyelid patch to be used for treatment of eyelid diseases by a steroid therapy usually contains steroid in a pressure-sensitive adhesive layer. In Patent Literature 2 (Japanese Patent Application Laid-Open No. S63-230635), a transdermal patch containing corticosteroid such as clobetasol in a pressure-sensitive adhesive layer, that is, a patch for treatment has been disclosed, however, a patch for treatment of eyelid diseases has not specifically suggested. Hereinafter, clobetasol or the acid ester thereof may be collectively simply referred to as "clobetasol". Therefore, a patch for treatment of eyelid diseases, which is provided with a pressure-sensitive adhesive layer containing clobetasol, is capable of applying on the skin of eyelid over a long period of time, and has less residual adhesive and is gentle to the skin, has been required. In addition, a patch for treatment of eyelid diseases which is unnoticeable in an applied state, has also been required.

In the above-mentioned Patent Literature 1, a patch in which a drug for eyelid diseases such as adrenal corticosteroid is mixed, that is, a transdermal drug delivery system for treatment of ophthalmic diseases has been described, and as a pressure-sensitive adhesive layer, a pressure-sensitive adhesive layer composed of a rubber-based pressure-sensitive adhesive, an acrylic pressure-sensitive adhesive, or a silicone-based pressure-sensitive adhesive has been disclosed.

Further, in Patent Literature 3 (Japanese Patent Application Laid-Open No. H05-17346), a patch for medical use, in which a pressure-sensitive adhesive layer including an adhesive basis that contains paraffinic hydrocarbon and/or naphthenic hydrocarbon and an alicyclic hydrocarbon resin, and a styrene-isoprene-styrene block copolymer, is provided on one surface of a support, has been disclosed, and as the support, a synthetic resin film such as polyester, polyethylene, polyvinyl chloride, polyvinylidene chloride, polyethylene-vinyl acetate copolymers, and polyurethane; nonwoven fabrics; cloth; aluminum foil; and the like have been mentioned, and also use of a soft vinyl chloride film with a thickness of 135 µm has been specifically disclosed. Furthermore, in Patent Literature 4 (WO 2006/092829), a patch for external use laminated with a pressure-sensitive adhesive layer in which a styrene-isoprene-styrene block copolymer, a tackifier resin, and a softening agent are mixed as essential components, and flurbiprofen is mixed as an active component, on a support, has been disclosed, and as the support, nonwoven fabrics and fabrics have been mentioned.

However, a conventional patch has not yet had sufficient effects as a patch for treatment of eyelid diseases, the improvement of the patch for treatment of eyelid diseases provided with a pressure-sensitive adhesive layer that contains clobetasol has been required. In addition, it is desirable that the amount of a drug such as steroid is kept to the minimum, and the high percutaneous permeability is realized. Therefore, a combination of a support and a pressure-sensitive adhesive layer appropriate for a patch for treatment of eyelid disease, which is provided with a pressure-sensitive adhesive layer that contains a small amount of clobetasol, is capable of applying on the skin of eyelid over a long hours, and has less residual adhesive and is gentle to the skin, has been required.

CITATION LIST

Patent Literature

[Patent Literature 1] WO 2004/064817
[Patent Literature 2] Japanese Patent Application Laid-Open No. S63-230635
[Patent Literature 3] Japanese Patent Application Laid-Open No. H05-17346
[Patent Literature 4] WO 2006/092829

SUMMARY OF INVENTION

Technical Problem

An object of the present invention is to provide a patch for treatment of eyelid disease that is provided with a pressure-sensitive adhesive layer containing clobetasol, is capable of applying on the skin of eyelid for a long period of time, and has less residual adhesive and is gentle to the skin.

Solution to Problem

The present inventors have carried out an extensive investigation with a view toward achieving the above object. As a result, the inventors found that the above object could be achieved by employing the optimum combination of a pressure-sensitive adhesive layer and a support.

That is, according to the present invention, provided is a patch for treatment of eyelid diseases that is provided with a support, a pressure-sensitive adhesive layer, and a release layer in this order, wherein (a) the pressure-sensitive adhesive layer includes the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained; and (b) the support has elastic modulus with a Young's modulus of 0.01 to 0.5 GPa.

Further, according to the present invention, as an embodiment, patches for treatment of eyelid diseases of the following (1) to (12) are provided.

(1) The patch for treatment of eyelid diseases described above, wherein the styrene-isoprene-styrene block copolymer has a styrene content of 15% by mass or more, and a diblock content of 30% by mass or less.

(2) The patch for treatment of eyelid diseases described above, wherein the pressure-sensitive adhesive layer further includes the following (a-2') and (a-3'):

(a-2') a ratio (mass ratio) of the styrene-isoprene-styrene block copolymer and the tackifier resin is 1:2.4 to 1:3.5; and (a-3') a content of the softening agent is 40% to 55% by mass.

(3) The patch for treatment of eyelid diseases described above, wherein the tackifier resin is a terpene resin.

(4) The patch for treatment of eyelid diseases described above, wherein the softening agent is liquid at room temperature.

(5) The patch for treatment of eyelid diseases described above, wherein the softening agent is liquid paraffin.

(6) The patch for treatment of eyelid diseases described above, wherein the support is a polyethylene film with a thickness of 1 to 80 μm.

(7) The patch for treatment of eyelid diseases described above, wherein a carrier film is provided on a surface of the opposite side of the pressure-sensitive adhesive layer side of the support.

(8) The patch for treatment of eyelid diseases described above, wherein the carrier film is a polyester film.

(9) The patch for treatment of eyelid diseases described above, wherein a surface of the support side of the carrier film is matt finished.

(10) The patch for treatment of eyelid diseases described above, wherein an applying area per sheet is 0.5 to 10 cm$^2$.

(11) The patch for treatment of eyelid diseases described above, wherein a shape is a rectangle, an ellipse, a crescent, a circle, a horseshoe, or a ring.

(12) The patch for treatment of eyelid diseases described above, wherein an accumulated amount penetrated into the skin of clobetasol or acid ester thereof is 1.0 to 3.0 μg/cm$^2$ in 24 hours in an in vitro percutaneous permeation test using a hairless mouse skin.

Further, according to the present invention, provided is a method for producing the above-described patch for treatment of eyelid diseases described above, containing: forming a pressure-sensitive adhesive layer on an upper surface of a release layer.

Advantageous Effects of Invention

According to the present invention, a patch for treatment of eyelid diseases that is provided with a support, a pressure-sensitive adhesive layer, and a release layer in this order, wherein (a) the pressure-sensitive adhesive layer includes the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained; and (b) the support has elastic modulus with a Young's modulus of 0.01 to 0.5 GPa; exerts the effects that a patch for treatment of eyelid diseases, which is capable of applying for a long period of time on the skin of eyelid where sebum is secreted, and has less residual adhesive, is gentle to the skin, and has excellent drug permeability at a low concentration, can be provided. Further, according to the present invention, the effect that the patch for treatment of eyelid diseases described above can be readily produced is exerted.

DESCRIPTION OF EMBODIMENTS

The patch for treatment of eyelid diseases according to the present invention is a patch for treatment of eyelid diseases that is provided with a support, a pressure-sensitive adhesive layer, and a release layer in this order, and has a feature of the combination of the support and the pressure-sensitive adhesive layer.

1. Support

The patch for treatment of eyelid diseases according to the present invention is provided with a support having elastic modulus with a Young's modulus of 0.01 to 0.5 GPa as the support.

As for the patch for treatment of eyelid diseases according to the present invention, by being provided with a support having elastic modulus with a Young's modulus of 0.01 to 0.5 GPa as the support, the patch for treatment of eyelid diseases can closely adhere to the skin of eyelid, and can have the flexibility to an extent capable of following to the movement of the eyelid. As a result, the patch for treatment of eyelid diseases, which can be applied for a long period of time on the skin of eyelid where sebum is secreted, and has less residual adhesive and is gentle to the skin, can be provided. Further, as will be described later, as the support, in many cases, a plastic film having substantially high transparency is used, and thus the patch for treatment of eyelid diseases, which is unnoticeable in an applied state, can be provided. When the Young's modulus of the support is too low, the strength of the patch for treatment of eyelid diseases is insufficient, and thus when the patch for treatment of eyelid diseases is applied on the eyelid or removed the patch for treatment of eyelid diseases after the required period of time, the patch may be broken. When the Young's modulus is too high, the patch for treatment of eyelid diseases cannot closely adhere to the skin of eyelid or cannot follow to the movement of eyelid, and thus the patch for treatment of eyelid diseases may not be applied for a long period of time.

The support provided to the patch for treatment of eyelid diseases according to the present invention is not particularly limited as long as the Young's modulus of the support is 0.01 to 0.5 GPa, preferably 0.03 to 0.48 GPa, and more preferably 0.05 to 0.45 GPa as the elastic modulus, however, in many cases, a plastic film having elastic modulus with a Young's modulus of 0.01 to 0.5 GPa is appropriately used. The Young's modulus of the plastic film is measured in accordance with ASTM-D-882, and the support provided to the patch for treatment of eyelid diseases according to the present invention has elastic modulus with a Young's modulus of 0.01 to 0.5 GPa in both directions of MD (an extrusion direction at the time of film forming) and TD (a direction perpendicular to the extrusion direction at the time of film forming) of the film.

As a plastic that is used as a material for the plastic film to be used as a support of a patch, there are synthetic resins including polyolefin such as polyethylene, and polypropylene; polyester such as polyethylene terephthalate, polybutylene terephthalate, and polyethylene naphthalate; polystyrene; polyamide such as nylon 6, nylon 66, and MXD6; polyvinyl alcohol; an ethylene-vinyl acetate copolymer; polyurethane such as acrylic polyurethane, polyester polyurethane, and polyether polyurethane; synthetic rubber such as a styrene-isoprene-styrene copolymer, a styrene-butadiene-styrene copolymer, a styrene-ethylene-propylene-styrene copolymer, and styrene-butadiene rubber; and the like; and a plastic film formed by using a synthetic resin composition in which various organic additives (may be resins) or inorganic additives are contained in the above synthetic resins, alone or in combination to mold the plastic film, and further a laminated body of the plastic film, are mentioned. As these plastic films, a nonoriented film, a uniaxial oriented film, a biaxially oriented film, or the like may be selected.

A plastic film having elastic modulus with a Young's modulus of 0.01 to 0.5 GPa that is appropriately used as the support of the patch for treatment of eyelid diseases according to the present invention can be prepared by selecting the composition of the material or selecting the conditions of forming so as to obtain a plastic film having the required Young's modulus as the elastic modulus by using a plastic such as the above-described synthetic resins as a main material.

Specifically, from the viewpoints of the easiness of the adjustment of Young's modulus, and the like, as a material, polyolefin such as polyethylene (low density polyethylene, high density polyethylene, linear low density polyethylene, and the like), and polypropylene; and polyamide such as nylon 6; can be preferably used, in particular, a polyethylene film, a polypropylene nonoriented film, a nonoriented polyamide film, and the like are suitable. Further, in the polyester film and the like, when the polyester is used alone, the Young's modulus may not be 0.01 to 0.5 GPa as the elastic modulus, however, according to the resin blend, the formulation of the additives, and the like, there may be a case that the Young's modulus is 0.01 to 0.5 GPa as the elastic modulus.

As a material for forming the support of the patch for treatment of eyelid diseases according to the present invention, preferable characteristics of the molecular weight, the melting point, the glass transition temperature, the melt viscosity, and the like in the synthetic resins are not particularly limited, and may be selected in a range that the obtained plastic film has elastic modulus with a Young's modulus of 0.01 to 0.5 GPa that is required for the support.

[Thickness of Support]

The thickness of the support that is provided to the patch for treatment of eyelid diseases according to the present invention is not particularly limited, however, is generally in a range of 1 to 80 µm, preferably 3 to 70 µm, more preferably 5 to 60 µm. Therefore, the most preferable support is a polyethylene film with a thickness of 5 to 60 µm. From the viewpoint of the unnoticeability or the relaxation of discomfort of the patch for treatment of eyelid diseases during the application, the thickness of the support can be reduced in a range to an extent of 2 to 20 µm, and preferably 5 to 20 µm. When the thickness of the support is too thin, the strength of the support is insufficient, and thus when the patch for treatment of eyelid diseases is applied on the eyelid or removed the patch for treatment of eyelid diseases from the facial surface, the support may be broken, and further the production of the support may become difficult. When the thickness of the support is too thick, the thickness of the patch for treatment of eyelid diseases becomes thick, as a result, the patch for treatment of eyelid diseases is hard to adhere along the skin surface of eyelid with fine irregularities such as sulcus cutis, and the applied state becomes noticeable, the discomfort easily increases, and the pain at the time of removing also increases. The thickness of the support is measured by using a dial thickness gage. In addition, the thickness of other layers of the patch for treatment of eyelid diseases is measured in the same way as described above.

[Additives]

In a synthetic resin composition for forming a plastic film that becomes a support, as needed, various organic additives or inorganic additives including a colorant such as pigment and dye, a stabilizer, an ultraviolet absorbent, a lubricant, and the like can be added. The content of these additives may be selected from the optimum range according to the kind of the additives, however, relative to 100 parts by mass of the synthetic resin that constitutes the plastic film, may often be in a range of generally 0.001 to 30 parts by mass, preferably 0.01 to 25 parts by mass, more preferably 0.1 to 20 parts by mass.

[Matt Finish]

When the patch for treatment of eyelid diseases is applied on the skin surface of eyelid, in order to improve the touch, the slippage, the appearance, and the like of the patch for treatment of eyelid diseases, there may be preferably a case that minute irregularities are formed on the back surface of the support (that means the surface positioned on the opposite side of the pressure-sensitive adhesive layer side of the support) that constitutes the patch for treatment of eyelid diseases. That is, the patch can be a patch in which the surface of the opposite side of the pressure-sensitive adhesive layer side of the support is matt finished. By performing the matt finish, a coefficient of dynamic friction on the surface of the support can be reduced to less than 1.0. Further, as will be described later, when the patch for treatment of eyelid diseases is produced, minute irregularities are formed on a surface of a carrier film by performing matt finish, and then a support is formed on the minute irregularities, and thus the minute irregularities can be transferred on the surface (back surface) of the support that is a plastic film.

Further, the support may be performed a surface treatment such as a sandblast treatment, and a corona treatment on one surface or both surfaces for the purpose of improving the anchoring with a pressure-sensitive adhesive. Furthermore, in order to easily take out the patch from the package, the irregularities can be provided on one surface or both surfaces of the support by a method other than the sandblast.

2. Pressure-Sensitive Adhesive Layer

The patch for treatment of eyelid diseases according to the present invention is characterized in that the pressure-sensitive adhesive layer includes the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained.

[Pressure-Sensitive Adhesive]

Generally, a pressure-sensitive adhesive layer of the patch is formed from a pressure-sensitive adhesive that shows pressure sensitive adhesion at ordinary temperature, as a pressure-sensitive adhesive that has weak skin irritation, for example, an acrylic pressure-sensitive adhesive, a natural rubber-based pressure-sensitive adhesive, a synthetic rubber-based pressure-sensitive adhesive, a silicone pressure-sensitive adhesive, a vinyl ester-based pressure-sensitive adhesive, a vinyl ether pressure-sensitive adhesive, an urethane pressure-sensitive adhesive, and the like, can be used. The pressure-sensitive adhesive forming the pressure-sensitive adhesive layer that is provided to the patch for treatment of eyelid diseases according to the present invention belongs to the category of a synthetic rubber-based pressure-sensitive adhesive.

The patch for treatment of eyelid diseases according to the present invention is a synthetic rubber-based pressure-sensitive adhesive in which as synthetic rubber, styrene-isoprene-styrene block copolymers are further contained. The patch for treatment of eyelid diseases according to the present invention is gentle to the skin, and is applied to adhere along the irregularities of the skin surface, thus the applied site is unnoticeable, and the tackiness is easily controlled so that the application can be maintained for a long period of time even on the area where sebum is secreted. Thus, the pressure-sensitive adhesive layer includes the special composition of the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained.

[Styrene-Isoprene-Styrene Block Copolymer]

In the patch for treatment of eyelid diseases according to the present invention, the pressure-sensitive adhesive layer contains a styrene-isoprene-styrene block copolymer. The styrene-isoprene-styrene block copolymer is not particularly limited as long as it is a styrene-isoprene-styrene block copolymer that is used in a synthetic rubber-based pressure-sensitive adhesive in a patch, for example, the styrene content in which is about 5% by mass or more. However, the styrene-isoprene-styrene block copolymer preferably contains a styrene-isoprene-styrene block copolymer in which the styrene content is 15% by mass or more and the diblock content is 30% by mass or less. The styrene content in the styrene-isoprene-styrene block copolymer is more preferably 17% by mass or more, and further preferably 20% by mass or more. The styrene content does not particularly have the upper limit, however, from the viewpoint of the viscoelasticity as the pressure-sensitive adhesive, is generally 30% by mass. The diblock content in the styrene-isoprene-styrene block copolymer is more preferably 25% by mass or less, and further preferably 20% by mass or less. The diblock content does not particularly have the lower limit, however, is generally 5% by mass from the problem of the synthesis. In the case that the styrene content is too low or the diblock content is too high in the styrene-isoprene-styrene block copolymer, when the patch for treatment of eyelid diseases is removed, the adhesive may be transferred, or the flare may be caused because of the increased skin stimulation. The preferably-used styrene-isoprene-styrene block copolymer in which the styrene content is 15% by mass or more and the diblock content is 30% by mass or less may be produced by polymerizing the styrene and the isoprene that are monomers while adjusting the polymerization conditions, or may be selected from the commercial products to be used. As the commercial product, for example, JSR SIS5002 (the styrene content is 22% by mass, and the diblock content is 15% by mass) and JSR SIS5000 (the styrene content is 14% by mass, and the diblock content is 26% by mass) that are manufactured by JSR Corporation, and the like are known. The styrene-isoprene-styrene block copolymer may be used by only one kind, or by several kinds in combination.

As a styrene-isoprene-styrene block copolymer that is contained in the pressure-sensitive adhesive layer of the patch for treatment of eyelid diseases according to the present invention, the styrene-isoprene-styrene block copolymer described above in which the styrene content is 15% by mass or more and the diblock content is 30% by mass or less may be used alone, or as long as the styrene-isoprene-styrene block copolymer described above in which the styrene content is 15% by mass or more and the diblock content is 30% by mass or less, is contained in an amount of 50% by mass or more, more preferably 70% by mass or more, further preferably 90% by mass or more of the styrene-isoprene-styrene block copolymer, other styrene-isoprene-styrene block copolymers may be used in combination.

The styrene content of the styrene-isoprene-styrene block copolymer can be measured by infrared spectroscopy, and the diblock content can be measured by a gel permeation chromatography (GPC) method.

The weight-average molecular weight of the styrene-isoprene-styrene block copolymer is generally in a range of 50,000 to 1,500,000, preferably 80,000 to 1,000,000, more preferably 100,000 to 400,000. By setting the weight-average molecular weight of the styrene-isoprene-styrene block copolymer in the above-described range, the cohesiveness, the adhesive force, the mixing activity with other components, and the affinity with other components can be well-balanced in the styrene-isoprene-styrene block copolymer. The weight-average molecular weight of the styrene-isoprene-styrene block copolymer is a value determined in terms of a value of standard polystyrene by a GPC method.

[Tackifier Resin]

The patch for treatment of eyelid diseases according to the present invention contains a styrene-isoprene-styrene block copolymer, a tackifier resin, and a softening agent, and has a ratio (mass ratio) of the styrene-isoprene-styrene block copolymer and the tackifier resin of 1:2 to 1:4. That is, by containing the tackifier resin 2 to 4 times the amount (mass ratio) of the styrene-isoprene-styrene block copolymer in the pressure-sensitive adhesive layer of the patch for treatment of eyelid diseases according to the present invention, the patch for treatment of eyelid diseases that can be applied over a long period of time on the skin of eyelid where sebum is secreted, and has less residual adhesive and is gentle to the skin, is provided. The ratio (mass ratio) of the styrene-isoprene-styrene block copolymer and the tackifier resin is preferably 1:2.2 to 1:3.8, and more preferably 1:2.4 to 1:3.5. When the proportion of the tackifier resin to the styrene-isoprene-styrene block copolymer is too low, the patch may not be able to be applied over a long period of time on the skin of eyelid where sebum is secreted. When the proportion of the tackifier resin is too high, the adhesive may be transferred at the time of removing the patch for treatment of eyelid diseases, or the flare may be caused because of the increased skin stimulation.

As the tackifier resin, the tackifier resin is not particularly limited as long as it is a tackifier resin that is generally used for a rubber-based pressure-sensitive adhesive, and one kind or multiple kinds can be mixed. For example, a terpene resin [for example, YS RESIN PX, and CLEARON P (hydrogenated terpene resin) manufactured by Yasuhara Chemical Co. Ltd., and the like], a rosin resin [for example, KE-311, KE-100, and SUPER ESTER S-100 (rosin ester) manufactured by Arakawa Chemical Industries, Ltd., FORAL 105 (hydrogenated rosin ester) manufactured by Pinova Inc., and the like], a coumarone-indene resin, a petroleum resin, an alicyclic saturated hydrocarbon resin [for example, ARKON (registered trademark) P-100 manufactured by Arakawa Chemical Industries, Ltd., and the like], hydrogenated alicyclic hydrocarbon (for example, ESCOREZ 5300 manufactured by Tonex Co., Ltd., and the like), are included. From the viewpoint of the cohesive force, a terpene resin is preferable.

[Softening Agent]

The pressure-sensitive adhesive layer of the patch for treatment of eyelid diseases according to the present invention contains a styrene-isoprene-styrene block copolymer, a tackifier resin, and a softening agent, and the content of the softening agent is 40% to 60% by mass. That is, by containing the softening agent in an amount of 40% to 60% by mass in the pressure-sensitive adhesive layer of the patch for treatment of eyelid diseases according to the present invention, the followability of the patch for treatment of eyelid diseases to the skin is improved, further the adhesive force is adjusted, and the skin stimulation can be reduced, therefore, a patch for treatment of eyelid diseases that can be applied over a long period of time on the skin of eyelid where sebum is secreted, and has less residual adhesive and is gentle to the skin, is provided. The content of the softening agent is preferably 40% to 58% by mass, and more preferably 40% to 55% by mass. When the proportion of the softening agent is too low, the followability of the patch for treatment of eyelid diseases to the skin of eyelid is reduced, and further the pain at the time of removing may be increased. When the proportion of the softening agent is too high, the adhesive may be transferred at the time of removing.

The softening agent is not particularly limited as long as it is a softening agent that is generally used for a rubber-based pressure-sensitive adhesive. For example, examples of the softening agent include liquid paraffin, liquid polybutene, liquid polyisobutylene, castor oil, cottonseed oil, palm oil, coconut oil, silicone oil, and process oil. From the viewpoint of showing the effective softening action, a softening action that is liquid at room temperature is preferable. Further, from the viewpoints of the safety and the compatibility with the styrene-isoprene-styrene block copolymer, liquid paraffin is particularly preferable.

[Clobetasol or Acid Ester Thereof]

The pressure-sensitive adhesive layer of the patch for treatment of eyelid diseases according to the present invention is characterized in that a predetermined amount and a predetermined proportion of a styrene-isoprene-styrene block copolymer, a tackifier resin, and a softening agent are contained, and further clobetasol or the acid ester thereof is contained in an amount of 0.005% to 5% by mass. The content of clobetasol or the acid ester thereof is preferably 0.05% to 3% by mass, and more preferably 0.1% to 2% by mass. When the content of the clobetasol or the acid ester thereof is too high, there is a risk of causing a side effect such as contact dermatitis, atrophoderma, and telangiectasis. The clobetasol or the acid ester thereof that can be contained in the pressure-sensitive adhesive layer of the patch for treatment of eyelid diseases means at least one kind selected from the group consisting of clobetasol, and the acid ester of clobetasol. As the clobetasol or the acid ester thereof, in addition to clobetasol, for example, butyrate, acetate, formate, propionate, or dipropionate ester of clobetasol, or the like can be used. Among these, acid ester of clobetasol such as clobetasol propionate, clobetasol butyrate, and clobetasol valerate is preferable in use.

[Other Drug]

The pressure-sensitive adhesive layer of the patch for treatment of eyelid diseases according to the present invention contains a predetermined amount and a predetermined proportion of a styrene-isoprene-styrene block copolymer, a tackifier resin, and a softening agent, further contains clobetasol or the acid ester thereof, and in addition can contain various additives as needed, particularly, can contain a drug other than the clobetasol or the acid ester thereof. As the other drug, the drug is not particularly limited as long as it is a drug that is used by being contained in a pressure-sensitive adhesive layer of a patch for treatment of eyelid diseases. For example, an antiinflammatory agent (pyridoxine dicaprylate, dipotassium glycyrrhizinate, pyridoxine dipalmitate, glycyrrhizic acid, diphenhydramine hydrochloride, cork tree bark extract, glycyrrhetinyl stearate, lysozyme chloride, aminocaproic acid, reishi mushroom extract, coix seed extract, melilot extract, peony extract, dong quai extract, dong quai root extract, cnidium rhizome extract, geranium herb extract, allantoin, arnica extract, and the like), an antibacterial agent (shikonin, hinokitiol, cedrol, benzalkonium chloride, benzethonium chloride, the photosensitive element 201, adipic acid, and the like), a sebum secretion inhibitor (estradiol, vitamin B2, vitamin B6, royal jelly extract, riboflavin, and the like), oil absorption porous powders (porous nylon powders, porous cellulose powders, and the like), a sebum absorbent (kaolin, talc, clay, zinc oxide, and the like), a keratin remover (salicylic acid, sulfur, bentonite, cyclodextrin, and the like), an antioxidant (dibutylhydroxytoluene, tocopherol acetate, ascorbic acid, benzoic acid, parabens, benzalkonium chloride, benzethonium chloride, and the like), a skin roughness improvement agent (arnica montana extract, licorice extract, retinol, dipotassium glycyrrhizinate, peony extract, sage leaf extract, loquat leaf extract, rosemary extract, and the like), an antioxidant (vitamins, butyl hydroxy toluene, and the like), various nonsteroidal antiinflammatory drugs, an antihistamine, a humectant, vitamins, a perfume bases, a beauty component, and the like are mentioned; and other steroid can be contained.

[Other Additives]

Further, the pressure-sensitive adhesive layer of the patch for treatment of eyelid diseases according to the present invention can contain other additives as needed. As the other additive, the additive is not particularly limited as long as it is an additive that is customarily used by being contained in a pressure-sensitive adhesive layer of a patch for treatment of eyelid diseases. For example, a percutaneous absorption enhancer, a filler, an ultraviolet absorbent, a solubilizer, a colorant, a plasticizer, and the like are mentioned. In particular, a percutaneous absorption enhancer is preferably contained, and aliphatic higher alcohol such as lauryl alcohol; fatty acid such as isostearic acid; alcohol amine such as diisopropanolamine; fatty acid ester such as isopropyl myristate, and isopropyl palmitate; polyoxyalkylene alkyl ether such as polyoxyethylene oleyl ether; and the like can be used.

[Thickness of Pressure-Sensitive Adhesive Layer]

The thickness of the pressure-sensitive adhesive layer of the patch for treatment of eyelid diseases according to the present invention is in a range of 1 to 50 μm, preferably 3 to 45 μm, and more preferably 5 to 40 μm. The pressure-sensitive adhesive layer provided to the patch for treatment of eyelid diseases according to the present invention includes the above-described following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained; and thus has appropriated tackiness, therefore, the patch for treatment of eyelid diseases that can be applied for a long period of time on the skin of eyelid where sebum is secreted, and has less residual adhesive and is gentle to the skin, can be provided. The pressure-sensitive adhesive layer provided to the patch for treatment of eyelid diseases according to the present invention further includes the following (a-2') and (a-3'):

(a-2') a ratio (mass ratio) of the styrene-isoprene-styrene block copolymer and the tackifier resin is 1:2.4 to 1:3.5; and (a-3') a content of the softening agent is 40% to 55% by mass; and thus more excellent effect can be exerted. [Thickness of Support and Pressure-Sensitive Adhesive Layer]

The patch for treatment of eyelid diseases according to the present invention has a total thickness of the support and the pressure-sensitive adhesive layer in a range of 2 to 120 μm, and preferably in a range of 6 to 100 μm, and more preferably 10 to 80 μm. When the total thickness of the support and the pressure-sensitive adhesive layer is too thin, the strength of the patch for treatment of eyelid diseases is insufficient, and thus at the time of applying the patch for treatment of eyelid diseases on the skin of eyelid or at the time of removing the patch for treatment of eyelid diseases from the skin of eyelid, the patch may be broken, and further the tackiness to the skin of eyelid becomes insufficient, and thus the adhesiveness to the facial surface where sebum is largely secreted may become insufficient. On the other hand, when the total thickness of the support and the pressure-sensitive adhesive layer is too thick, the patch for treatment of eyelid diseases is hard to adhere along the fine irregularities on the skin surface of eyelid such as sulcus cutis, and the applied state becomes noticeable, the discomfort easily increases, and at the time of removing the patch for treatment of eyelid diseases from the skin of eyelid, the skin may be damaged, or the pain may be felt.

3. Release Layer

The patch for treatment of eyelid diseases according to the present invention is a patch for treatment of eyelid diseases that is provided with a support, a pressure-sensitive adhesive layer, and a release layer in this order. That is, the patch for treatment of eyelid diseases according to the present invention is provided with a release layer adjacent to the pressure-sensitive adhesive layer in order to protect the pressure-sensitive adhesive layer until the patch for treatment of eyelid diseases, specifically the pressure-sensitive adhesive layer is applied onto the skin.

As the release layer of the present invention, the release layer is not particularly limited, in a technical field of a patch for treatment of eyelid diseases and further a patch (pressure-sensitive adhesive tape), generally the one that is used under the name of released paper, mold releasing film, release paper, releasing film, release liner, and the like can be employed. Specifically, for example, a polyethylene terephthalate film, the surface of which was subjected to a silicone treatment; a laminated body of the polyethylene, the surface of which was subjected to a silicone treatment, and paper; and the like are mentioned. The release layer may protect the pressure-sensitive adhesive layer as two or more of the sheets that have the same thickness or different thickness from each other. Further, the release layer may have a break in order to improve the handling (that is, the detachability from the pressure-sensitive adhesive layer), or may be formed larger than the area of the patch for treatment of eyelid diseases, and thus provided with a grip section in the periphery thereof. Further, for the purpose of improvement of the handling, improvement of the printability, or the like, the release layer may have irregularities by a sandblast treatment and the like provided on a surface of the release layer, which faces the pressure-sensitive adhesive layer, or on a surface of the opposite side of the pressure-sensitive adhesive layer side. Further, the release layer is provided as one large sheet, on which a combination of a pressure-sensitive adhesive layer, a support, and a carrier film may be arranged in a plural number, in this case, the release layer is shared by the plural number of the patches.

Further, the release layer, as will be described later, can be used for easily forming the pressure-sensitive adhesive layer in a method for producing the patch for treatment of eyelid diseases according to the present invention. That is, on a surface of the release layer prepared in advance, by a method for applying the adhesive composition that contains a styrene-isoprene-styrene block copolymer, a tackifier resin, and a softening agent, which are used for forming a pressure-sensitive adhesive layer, and the like, a laminating sheet that is provided with a pressure-sensitive adhesive layer and a release layer is produced, then a support is laminated on a surface of the pressure-sensitive adhesive layer, and thus a patch for treatment of eyelid diseases that is provided with a support, a pressure-sensitive adhesive layer, and a release layer in this order can be obtained.

The thickness of the release layer can be appropriately determined, and is not particularly limited, however, generally 20 μm or more, and preferably 40 μm or more, and the upper limit is about 500 μm.

4. Carrier Film

The patch for treatment of eyelid diseases according to the present invention is a patch for treatment of eyelid diseases that is provided with a support, a pressure-sensitive adhesive layer, and a release layer in this order. Further, by providing a carrier film that is adjacent to a support, on a surface of the opposite side of the pressure-sensitive adhesive layer side of the support, the handling of the patch for treatment of eyelid diseases, and the applying characteristics to the skin can be improved. That is, when the patch for treatment of eyelid diseases is applied, wrinkles may form in the support, or the patch for treatment of eyelid diseases may bend over and the pressure-sensitive adhesive layer may adhere to each other, however, by providing a carrier film adjacent to the support of the patch for treatment of eyelid diseases, when the patch for treatment of eyelid diseases is provided with a carrier film, a support, a pressure-sensitive adhesive layer, and a release layer in this order, the shape retention of the patch for treatment of eyelid diseases is improved, and thus such a problem can be prevented. A carrier film is used such that the carrier film is removed from the support after at first, removing the release layer from the above-described patch for treatment of eyelid diseases, and applying the patch for treatment of eyelid diseases while pressing the pressure-sensitive adhesive layer against the skin of eyelid.

The material for forming the carrier film is not particularly limited, and a material similar to the material for forming the above-described release layer can be used. For example, the carrier film can be formed by using a film composed of various thermoplastic resins, for example, a film composed of polyurethane, polyethylene, polypropylene, ionomer, polyamide, polyvinyl chloride, polyvinylidene chloride, ethylene-vinyl acetate copolymers, thermoplastic polyester, polytetrafluoroethylene, and the like can be used. Further, a laminated body of these films and paper can be used. A carrier film is preferably a polyester film, from the viewpoint of the handling or the improvement of the applying characteristics to the skin. Further, in order to easily remove the carrier film from the support after applying of the patch for treatment of eyelid diseases, matt finish is preferably performed on a surface of the side of the support. The carrier film and the support are formed releasably by thermocompression bonding, adhesion, or the like. In order to adjust the peel force of the carrier film and the support, a pressure-sensitive adhesive, a liquid plasticizer, a mold releasing agent, and the like may be applied on a surface of the carrier film, which faces the support, or other surface treatments may be performed.

The thickness of the carrier film can be appropriately determined, and is not particularly limited, however, generally 20 µm or more, and preferably 40 µm or more, and the upper limit is about 500 µm.

[Size of Carrier Film]

When the patch for treatment of eyelid diseases according to the present invention is provided with a carrier film, the size of the carrier film may be the same as that of the support, or may be larger than that of the support. When the carrier film is larger than the support, by using the carrier film as a grip section of the patch, the pressure-sensitive adhesive layer of the patch for treatment of eyelid diseases can be easily removed from the release layer, further, without touching the pressure-sensitive adhesive with fingers, the pressure-sensitive adhesive layer of the patch for treatment of eyelid diseases can be applied onto the skin. Herein, "the carrier film is larger than the support" means the state that the whole area of the carrier film does not cover the support, in other words, means the state that the carrier film has some area not covering the support. For example, in addition to the aspect of a case that the area of the carrier film is larger than the area of the support (in this case, part of the carrier film covers the support), an aspect such as a case that the carrier film is formed into a pattern form such as a latticed pattern, and the edge of the lattice is protruded from the support, a case that the carrier film covers the support such that the marginal part of the support is protruded from the support, or the like, can be taken to be provided. The carrier film may be provided to cover such that the support is divided into multiple sheets, or is in a state of partially being overlapped. Further, on the upper surface of the carrier film (on the surface of the opposite side of the support side), a sheet provided with the leading or the nick may be arranged in order to further improve the handling.

[Peel Force of Release Layer and Peel Force of Carrier Film]

A force (peel force of the release layer) required to remove the release layer from the pressure-sensitive adhesive layer of the patch for treatment of eyelid diseases is set weaker than the force (peel force of the carrier film) removing the carrier film from the support of the patch for treatment of eyelid diseases. By setting the force as described above, after removing the release layer from the pressure-sensitive adhesive layer of the patch for treatment of eyelid diseases, the carrier film is left integrally on the support, therefore, until the patch for treatment of eyelid diseases is applied on the skin, the patch for treatment of eyelid diseases has a certain degree of rigidity, and thus can be good for the handling.

5. Patch for Treatment of Eyelid Diseases

The patch for treatment of eyelid diseases according to the present invention is a patch for treatment of eyelid diseases that is provided with a support, a pressure-sensitive adhesive layer, and a release layer in this order, wherein (a) the pressure-sensitive adhesive layer includes the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained; and (b) the support has elastic modulus with a Young's modulus of 0.01 to 0.5 Gpa. The patch for treatment of eyelid diseases according to the present invention can exert the effects that the patch for treatment of eyelid diseases, which can be applied for a long period of time on the skin of eyelid where sebum is secreted by specifically combining the pressure-sensitive adhesive layer and the support provided with the above-described constitution, and has less residual adhesive and is gentle to the skin, and has excellent drug permeability at a low concentration, is provided. In particular, when the above-described styrene-isoprene-styrene block copolymer includes a styrene-isoprene-styrene block copolymer in which a styrene content is 15% by mass or more and a diblock content is 30% by mass or less, more excellent effect can be exerted.

The patch for treatment of eyelid diseases according to the present invention is used by applying on a skin surface of eyelid, in order to percutaneously administer to ophthalmic topical tissue the clobetasol or the acid ester thereof that is a remedy for ophthalmic diseases contained in the pressure-sensitive adhesive layer. The skin surface of eyelid means a front surface (skin surface) of an upper eyelid, a lower eyelid or both eyelids, or skin surfaces of these eyelids and the skin surfaces therearound. Therefore, the patch for treatment of eyelid diseases according to the present invention preferably has a shape and a size that are capable of being applied along a skin surface of the upper eyelid, the lower eyelid or both eyelids. Specific examples of such a shape include shapes such as a rectangle, an ellipse, a crescent, a circle, a horseshoe, and a ring along the form of the front surface of the eyelid. The thickness of the patch for treatment of eyelid diseases according to the present invention (the total thickness of the support, the pressure-sensitive adhesive layer, and the release layer) is generally in a range of 22 to 400 μm, and in many cases 40 to 300 μm.

The patch for treatment of eyelid diseases according to the present invention is good in the adhesiveness and the flexibility, has less pain at the time of removing and less residual adhesive after the removing. Further, more specifically, the patch for treatment of eyelid diseases according to the present invention can confirm the effects by the adhesive force measured by a predetermined method, probe tack, the area of removed corneocyte, and a percutaneous permeation test of the clobetasol or the acid ester thereof.

[Adhesiveness]

The patch for treatment of eyelid diseases according to the present invention is excellent in the adhesiveness that is evaluated by the following methods. That is, test specimens (a rectangle with an area of 2 cm$^2$) that have been cut out into a size of width 10 mm×length 20 mm from the patch for treatment of eyelid diseases according to the present invention are applied on the lower eyelids that have been wiped off the water after the face-wash of the subjects who are 7 adults of both sexes, and the evaluations of the adhesiveness 12 hours after the standing (hereinafter, may be referred to as "12 hours after the applying") are collected. In the light of the following criteria, the adhesiveness of the patch for treatment of eyelid diseases is evaluated. If the evaluation is AA or A, the adhesiveness of the patch for treatment of eyelid diseases can be said to be excellent.

<Evaluation Criteria of Adhesiveness>
  AA: 6 to 7 subjects evaluated the adhesiveness as strong.
  A: 4 to 5 subjects evaluated the adhesiveness as strong.
  B: 2 to 3 subjects evaluated the adhesiveness as strong.
  C: 1 or 0 subject evaluated the adhesiveness as strong.

[Flexibility]

The patch for treatment of eyelid diseases according to the present invention is excellent in the flexibility that is evaluated by the following methods. That is, the evaluations of the flexibility 12 hours after the applying are collected from 7 subjects to whom the test specimens of the above-described patch for treatment of eyelid diseases were applied. In the light of the following criteria, the flexibility of the patch for treatment of eyelid diseases is evaluated. If the evaluation is AA or A, the flexibility of the patch for treatment of eyelid diseases can be said to be excellent.

<Evaluation Criteria of Flexibility>
  AA: 6 to 7 subjects evaluated that there was flexibility.
  A: 4 to 5 subjects evaluated that there was flexibility.
  B: 2 to 3 subjects evaluated that there was flexibility.
  C: 1 or 0 subject evaluated that there was flexibility.

[Pain at the Time of Removing]

The patch for treatment of eyelid diseases according to the present invention is excellent in the point that the pain at the time of removing, which is evaluated by the following methods, is less. That is, the evaluations of the presence or absence of the pain at the time of removing 12 hours after the applying are collected from 7 subjects to whom the test substances of the above-described patch for treatment of eyelid diseases were applied. The pain at the time of removing is evaluated on the following 4-point scale: 0 (Feel no pain), 1 (Feel a little pain), 2 (Feel a pain stronger than 1), 3 (Feel a pain strongly), and the average value of 7 subjects is rounded. In the light of the following criteria, the pain at the time of removing of the patch is evaluated. If the evaluation is AA or A, the pain at the time of removing is less and can be said to be excellent.

<Evaluation Criteria of Pain at the Time of Removing>
  AA: The average value on the 4-point scale was 0.
  A: The average value on the 4-point scale was 1.
  B: The average value on the 4-point scale was 2.
  C: The average value on the 4-point scale was 3.

[Residual Adhesive after the Removing]

The states of the residual adhesive on the lower eyelids to which the above-described patch for treatment of eyelid diseases were applied (hereinafter, may be simply referred to as "residual adhesive") of the 7 subjects to whom the test specimens of the patch for treatment of eyelid diseases were applied, after removing the patch for treatment of eyelid diseases 12 hours after applying the patch for treatment of eyelid diseases, are visually observed. The residual adhesive after the removing is evaluated on the following 4-point scale: 0 (No residual adhesive), 1 (Observed residual adhesive slightly), 2 (Observed more residual adhesive than 1), 3 (Observed residual adhesive frequently), and the average value of 7 subjects is rounded. In the light of the following criteria, the residual adhesive of the patch for treatment of eyelid diseases is evaluated. If the evaluation of the residual adhesive is AA or A, the usability of the patch for treatment of eyelid diseases can be said to be excellent.

<Evaluation Criteria of Residual Adhesive>
  AA: The average value on the 4-point scale was 0.
  A: The average value on the 4-point scale was 1.
  B: The average value on the 4-point scale was 2.
  C: The average value on the 4-point scale was 3.

[Adhesive Force]

The patch for treatment of eyelid diseases according to the present invention has an adhesive force in a range of 0.5 to 3 N/15 mm, preferably 0.5 to 2.7 N/15 mm, more preferably 0.6 to 2.5 N/15 mm in a 180-degree peel test against a BA-SUS plate (bright annealed stainless steel) in accordance with Japanese Industrial Standards (JIS) Z0237. The patch for treatment of eyelid diseases according to the present invention has an adhesive force against a BA-SUS plate in the above-described range, and thus when the patch for treatment of eyelid diseases is applied on the skin of eyelid, the patch for treatment of eyelid diseases is not easily peeled off by an external force such as the movement of the eyelid, and at the same time, when the patch for treatment of eyelid diseases is removed from the skin surface of eyelid, the resistance or the pain is not felt. When the adhesive force against a BA-SUS plate is too high, the resistance or the pain may be felt at the time of removing the patch for treatment of eyelid diseases from the skin surface of eyelid. The 180-degree peel test against a BA-SUS plate measures the adhesive force at the time of tearing off the test specimen that had been cut out into a width of 15 mm from the patch for treatment of eyelid diseases, and was attached to a BA-SUS plate, and on which the coming and going was performed twice by a rubber roll with 2 kg at a speed of 300 mm/min, under the condition of peel rate at 300 mm/min in the 180 degrees direction in a minute by an Instron type tensile testing machine (the average value of n=3).

[Probe Tack]

The patch for treatment of eyelid diseases according to the present invention has a probe tack of the pressure-sensitive adhesive layer preferably in a range of 1.5 to 5 N/5 mmϕ, and more preferably 1.6 to 4 N/5 mmϕ. When the patch for treatment of eyelid diseases is applied on the skin of eyelid, by having a probe tack of the pressure-sensitive adhesive layer in the above-described range, the patch for treatment of eyelid diseases is not easily peeled off by an external force such as the movement of the eyelid, and at the time of removing the patch for treatment of eyelid diseases from the skin, there is no risk that the resistance or the pain is felt. The above-described probe tack is determined by using a probe tack tester manufactured by Nichiban Co., Ltd. in accordance with a probe tack test method that is described in JIS Z0237 (the 1996 edition) as reference, and measuring the strength required to tear off a cylindrical probe with a diameter of 5 mm in a vertical direction from the adhesive face (the average value of n=3).

[Area of Removed Corneocyte]

The patch for treatment of eyelid diseases according to the present invention can be applied over a long period of time on the skin of eyelid, and further has less residual adhesive and is gentle to the skin, and the area of removed corneocyte at the time of removing the patch for treatment of eyelid diseases from the skin of eyelid to which the patch for treatment of eyelid diseases is applied is 45% or less, preferably 40% or less, and more preferably 35% or less. The area of removed corneocyte of the patch for treatment of eyelid diseases is measured by the following method. That is, test specimens that were cut out into a size of width 10 mm×length 20 mm from the patch for treatment of eyelid diseases according to the present invention are applied on the lower eyelids that were wiped off the water after the face-wash of the subjects who are 7 adults of both sexes, and the test specimens are removed 12 hours after the standing, and then the total of the area of removed corneocyte that adhered to (the pressure-sensitive adhesive layer of) the patch for treatment of eyelid diseases is measured after the removing, and the ratio to the area of the patch is calculated (unit: %).

[Percutaneous Permeation Test of Clobetasol or Acid Ester Thereof]

The patch for treatment of eyelid diseases according to the present invention is a patch that is excellent in percutaneous permeability of clobetasol or the acid ester thereof. The penetrated amount into the skin of clobetasol or the acid ester thereof is measured by the following method. That is, in an in vitro percutaneous permeability test using a hairless mouse skin, the accumulated amount of clobetasol or the acid ester thereof, which is penetrated into the skin, is 1.0 to 3.0 µg/cm$^2$ in 24 hours. In an in vitro percutaneous permeability test using a hairless mouse skin, the accumulated amount of clobetasol or the acid ester thereof, which is penetrated into the skin, is preferably 1.1 to 2.8 µg/cm$^2$ and more preferably 1.2 to 2.5 µg/cm$^2$ in 24 hours. The in vitro percutaneous permeability test using a hairless mouse skin is performed by the following method. That is, an abdominal skin of a hairless mouse (male, 7 weeks old) is mounted on a horizontal diffusion cell having a diameter of 20 mmφ with the dermis side on the receptor layer side. Warm water at a temperature of 32° C. is circulated in a cell of double structure, and the inside of the cell is kept at a certain temperature condition. On the stratum corneum side of the skin, the patch for treatment of eyelid diseases that is punched out to 15 mmφ is applied. On the receiver side, a receiver solution (20% by mass of polyethylene glycol/purified water) is impregnated, while stirring with a stirring bar, every 6 hours from the beginning of the application the receiver solution is sampled by 1.0 mL, and methanol is added to each sampled receiver solution sample by 0.5 mL, the resultant is stirred and centrifuged to deproteinize. The deproteinized solution is quantified by HPLC (high performance liquid chromatography), and the concentration of clobetasol or the acid ester thereof is measured, and thus the accumulated amount (µg/cm$^2$) of clobetasol or the acid ester thereof, which is penetrated into the skin, is determined in 6, 12, and 24 hours, and each average value is determined (n=3). Further, in the horizontal diffusion cell after the sampling, an equivalent amount of the receiver solution is replenished.

[Shape and Size of Patch]

The patch for treatment of eyelid diseases according to the present invention is a patch for treatment of eyelid diseases that is provided with a support, a pressure-sensitive adhesive layer, and a release layer in this order, further, as long as the patch for treatment of eyelid diseases has the above-described characteristics, the shape and size thereof is not particularly limited, and the patch may be a patch for treatment of eyelid diseases with a predetermined shape, a patch for treatment of eyelid diseases with a roll state, or further a patch for treatment of eyelid diseases enclosed in a bag. Preferably, the patch for treatment of eyelid diseases is the one with a shape of a rectangle, an ellipse, a crescent, a circle, a horseshoe, a ring, or the like along the form of the front surface of eyelid. Further, in the patch for treatment of eyelid diseases that has a predetermined shape with a corner on the periphery thereof, the corner on the periphery may be appropriately rounded off. The size is not particularly limited, however, the applying area per sheet may be generally in a range of 0.5 to 10 cm$^2$, preferably 1 to 5 cm$^2$, and more preferably 1 to 3 cm$^2$.

6. A Method for Producing the Patch for Treatment of Eyelid Diseases

The patch for treatment of eyelid diseases according to the present invention is a patch for treatment of eyelid diseases that is provided with a support, a pressure-sensitive adhesive layer, and a release layer in this order, wherein (a) the pressure-sensitive adhesive layer includes the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained; and (b) the support has elastic modulus with a Young's modulus of 0.01 to 0.5 Gpa. As long as the above-described patch for treatment of eyelid diseases can be obtained, the method for producing the patch for treatment of eyelid diseases is not limited. From the viewpoint of the producibility, a method for producing the patch for treatment of eyelid diseases containing a step of forming the pressure-sensitive adhesive layer on an upper surface of the release layer is preferable. Specifically, a method in which while allowing the release layer that has been formed in advance to run in one direction, on a upper surface of the release layer, a pressure-sensitive adhesive forming the pressure-sensitive adhesive layer, that is, a pressure-sensitive adhesive containing a styrene-isoprene-styrene block copolymer, a tackifier resin, and a softening agent, and further clobetasol or the acid ester thereof, is coated, dry removal is performed and thus a pressure-sensitive adhesive layer is formed, and then a support having elastic modulus with a Young's modulus of 0.01 to 0.5 GPa (may be the one on which a carrier film is laminated) is laminated, is preferable.

The patch for treatment of eyelid diseases according to the present invention may be obtained, for example, as a patch for treatment of eyelid diseases with a roll state, according to the above-described method, in which one that is provided with a carrier film, a support, a pressure-sensitive adhesive layer, and a release layer in this order is produced, and then the one may be wound into a roll state; or the patch for treatment of eyelid diseases may be obtained in a predetermined size and shape, for example, by cutting out into a shape such as a rectangle, an ellipse, a crescent, a circle, a horseshoe, and a ring along the form of the front surface of the eyelid. Further, the patch for treatment of eyelid diseases may be obtained by further subsequently being enclosed in a bag. In order to maintain the stability of the drug, the air in a bag may be substituted with nitrogen, as needed.

EXAMPLES

Hereinafter, the present invention is specifically explained by referring to Examples and Comparative Examples, however, the present invention is not limited at all by these Examples. The measuring method of the characteristics and properties of the patch for treatment of eyelid diseases according to the present invention and each layer provided to the patch is as follows.
[Thickness]
Each thickness of the patch for treatment of eyelid diseases; and a carrier film, a support, a pressure-sensitive adhesive layer, and a release layer that were provided to the patch for treatment of eyelid diseases, was measured by using a dial thickness gage.
[Young's Modulus]
The Young's modulus of the support was measured in accordance with ASTM-D-882.
[Styrene Content and Diblock Content]
The styrene content of the styrene-isoprene-styrene block copolymer was measured by infrared spectroscopy, and the diblock content was measured by a GPC method.
[Adhesiveness]
The adhesiveness of the patch for treatment of eyelid diseases was evaluated by the following method. That is, test specimens (a rectangle with an area of 2 cm$^2$) that had been cut out into a size of width 10 mm×length 20 mm from the patch for treatment of eyelid diseases were applied on the lower eyelids that had been wiped off the water after the face-wash of the subjects who were 7 adults of both sexes, and the evaluations of the adhesiveness 12 hours after the standing (12 hours after the applying) were collected. In the light of the following criteria, the adhesiveness of the patch for treatment of eyelid diseases was evaluated.
<Evaluation Criteria of Adhesiveness>
  AA: 6 to 7 subjects evaluated the adhesiveness as strong.
  A: 4 to 5 subjects evaluated the adhesiveness as strong.
  B: 2 to 3 subjects evaluated the adhesiveness as strong.
  C: 1 or 0 subject evaluated the adhesiveness as strong.
[Flexibility]
The flexibility of the patch for treatment of eyelid diseases was evaluated by the following method. That is, from the 7 subjects to whom the test specimens of the above-described patch for treatment of eyelid diseases had been applied, the evaluations of the flexibility 12 hours after the applying were collected. In the light of the following criteria, the flexibility of the patch for treatment of eyelid diseases was evaluated.
<Evaluation Criteria of Flexibility>
  AA: 6 to 7 subjects evaluated that there was flexibility.
  A: 4 to 5 subjects evaluated that there was flexibility.
  B: 2 to 3 subjects evaluated that there was flexibility.
  C: 1 or 0 subject evaluated that there was flexibility.
[Pain at the Time of Removing]
The pain at the time of removing of the patch for treatment of eyelid diseases was evaluated by the following method. That is, from the 7 subjects to whom the test specimens of the above-described patch for treatment of eyelid diseases had been applied, the evaluations of the presence or absence of the pain at the time of removing 12 hours after the applying were collected. The pain at the time of removing the patch was evaluated on the following 4-point scale: 0 (Feel no pain), 1 (Feel a little pain), 2 (Feel a pain stronger than 1), 3 (Feel a pain strongly), and the average value of 7 subjects was rounded. In the light of the following criteria, the pain at the time of removing the patch was evaluated.
<Evaluation Criteria of Pain at the Time of Removing>
  AA: The average value on the 4-point scale was 0.
  A: The average value on the 4-point scale was 1.
  B: The average value on the 4-point scale was 2.
  C: The average value on the 4-point scale was 3.
[Residual Adhesive after the Removing]
The residual adhesive after the removing of the patch for treatment of eyelid diseases was evaluated by the following method. That is, the states of the residual adhesive on the lower eyelids to which the above-described patch for treatment of eyelid diseases had been applied of the 7 subjects to whom the test specimens of the patch for treatment of eyelid diseases had been applied, after removing the patch for treatment of eyelid diseases 12 hours after applying the patch for treatment of eyelid diseases, were visually observed. The state of the residual adhesive r was evaluated on the following 4-point scale: 0 (No residual adhesive), 1 (Observed residual adhesive slightly), 2 (Observed more residual adhesive r than 1), 3 (Observed residual adhesive frequently), and the average value of 7 subjects was rounded. In the light of the following criteria, the residual adhesive of the patch for treatment of eyelid diseases was evaluated.
<Evaluation Criteria of Residual Adhesive>
  AA: The average value on the 4-point scale was 0.
  A: The average value on the 4-point scale was 1.
  B: The average value on the 4-point scale was 2.
  C: The average value on the 4-point scale was 3.
[Adhesive Force (Adhesive Force Against a BA-SUS Plate)]
The adhesive force of the patch for treatment of eyelid diseases (adhesive force against a BA-SUS plate) was measured by performing a 180-degree peel test in accordance with JIS Z0237. That is, the adhesive force at the time of tearing off the test specimen of the patch for treatment of eyelid diseases, which had been cut out into a size of width 15 mm×length 70 mm, was attached to a BA-SUS plate, and on which the coming and going was performed twice by a rubber roll with 2 kg at a speed of 300 mm/min under the condition of a peel rate at 300 mm/min in the 180 degrees direction in a minute by an Instron type tensile testing machine was measured (unit: N/15 mm) (the average value of n=3).
[Probe Tack of the Pressure-Sensitive Adhesive Layer of the Patch for Treatment of Eyelid Diseases]
The probe tack of the pressure-sensitive adhesive layer of the patch for treatment of eyelid diseases was determined by using a probe tack tester manufactured by Nichiban Co., Ltd. in accordance with a probe tack test method described in JIS Z0237 (the 1996 edition) as reference, and measuring the strength required to tear off a cylindrical probe with a diameter of 5 mm in a vertical direction from the adhesive face (the average value of n=3).
[Area of Removed Corneocytes]
As for the area of removed corneocyte of the patch for treatment of eyelid diseases, test specimens that had been cut out into a size of width 10 mm×length 20 mm from the patch for treatment of eyelid diseases were applied on the lower eyelids that had been wiped off the water after the face-wash of the subjects who were 7 adults of both sexes, and the test specimens were removed 12 hours after the standing, and then the total of the area of the corneocytes that had adhered to (the pressure-sensitive adhesive layer of) the patch for treatment of eyelid diseases after the removing was measured, and the ratio to the area of the patch was calculated (unit: %).

[Percutaneous Permeation Test of Clobetasol or Acid Ester Thereof]

An abdominal skin of a hairless mouse (male, 7 weeks old) was mounted on a horizontal diffusion cell having a diameter of 20 mmφ with the dermis side on the receptor side. Warm water at a temperature of 32° C. was circulated in a cell of double structure, and the inside of the cell was kept at a certain temperature condition. On the stratum corneum side of the skin, the patch for treatment of eyelid diseases that had been punched out to 15 mmφ was applied. On the receiver side layer, a receiver solution (20% by mass of polyethylene glycol/purified water) was impregnated, while stirring with a stirring bar, every 6 hours from the beginning of the application the receiver solution was sampled by 1.0 mL, and methanol was added to each sampled receiver solution sample by 0.5 mL, the resultant was stirred and centrifuged to deproteinize. The deproteinized solution was quantified by HPLC (high performance liquid chromatography), and the concentration of clobetasol or the acid ester thereof was measured, and thus the accumulated amount ($\mu g/cm^2$) of clobetasol or the acid ester thereof, which had been penetrated into the skin, was determined in 6, 12, and 24 hours, and each average value ("an accumulated amount penetrated into the skin in 6 hours", "an accumulated amount penetrated into the skin in 12 hours", and "an accumulated amount penetrated into the skin in 24 hours") was determined (n=3). Further, in the horizontal diffusion cell after the sampling, an equivalent amount of the receiver solution was replenished.

Example 1

100 parts by mass of a styrene-isoprene-styrene block copolymer (JSR SIS5002 manufactured by JSR Corporation, the styrene content of 22% by mass, and the diblock content of 15% by mass), 250 parts by mass of a terpene resin (YS RESIN manufactured by Yasuhara Chemical Co. Ltd.) that was a tackifier resin, and 350 parts by mass of liquid paraffin [HICALL (registered trademark) M-352 manufactured by Kaneda Co., Ltd.] that was a softening agent; and clobetasol propionate at a proportion amount in which the content of clobetasol propionate in a pressure-sensitive adhesive layer was 0.7% by mass (in Example 1, 5 parts by mass) were mixed, and the mixture was dissolved in a solution of toluene/acetone=8/2, and thus a coating fluid to form a pressure-sensitive adhesive layer with a solid content of 57% by mass was prepared. The coating fluid was applied on one surface of the release paper (a siliconized polyethylene terephthalate film, thickness of 75 μm) that forms a release layer so as to give a coat thickness of 20 μm after drying, by using a bar coater, then the surface was dried, and thus a laminated body composed of a release layer and a pressure-sensitive adhesive layer was obtained. Subsequently, the patch for treatment of eyelid diseases with a thickness of 130 μm, in which on a upper surface of the pressure-sensitive adhesive layer, as a support, a low density polyethylene film (the Young's modulus of 0.12 GPa) with a thickness of 35 μm was carried and laminated, and then the support, the pressure-sensitive adhesive layer, and the release layer were provided in this order, was produced. As for this patch for treatment of eyelid diseases, the results of the measurements and evaluations of the adhesiveness, the flexibility, the pain at the time of removing, the residual adhesive after the removing, the adhesive force against a BA-SUS plate, the probe tack, and the area of removed corneocyte (hereinafter, may be collectively referred to as "characteristics"), and the composition of the pressure-sensitive adhesive layer are shown in Table 1.

Example 2

A patch for treatment of eyelid diseases was produced in the same manner as in Example 1 except that 300 parts by mass of liquid paraffin that was a softening agent were contained. Further, clobetasol propionate was mixed at a proportion amount in which the content of clobetasol propionate in a pressure-sensitive adhesive layer was 0.7% by mass. In the following Examples and Comparative Examples, the same manner as described above was applied. As for this patch for treatment of eyelid diseases, the results of the measurements and evaluations of the characteristics, and the composition of the pressure-sensitive adhesive layer are shown in Table 1.

Example 3

A patch for treatment of eyelid diseases was produced in the same manner as in Example 1 except that 250 parts by mass of liquid paraffin that was a softening agent were contained. As for this patch for treatment of eyelid diseases, the results of the measurements and evaluations of the characteristics, and the composition of the pressure-sensitive adhesive layer are shown in Table 1.

Example 4

A patch for treatment of eyelid diseases was produced in the same manner as in Example 2 except that the support was changed to a low density polyethylene film (the Young's modulus of 0.13 GPa) with a thickness of 15 μm. As for this patch for treatment of eyelid diseases, the results of the measurements and evaluations of the characteristics, and the composition of the pressure-sensitive adhesive layer are shown in Table 1.

Example 5

A patch for treatment of eyelid diseases was produced in the same manner as in Example 2 except that 100 parts by mass of a styrene-isoprene-styrene block copolymer (JSR SIS5000 manufactured by JSR Corporation, the styrene content of 14% by mass, and the diblock content of 26% by mass) were contained. As for this patch for treatment of eyelid diseases, the results of the measurements and evaluations of the characteristics, and the composition of the pressure-sensitive adhesive layer are shown in Table 1.

Example 6

A patch for treatment of eyelid diseases was produced in the same manner as in Example 1 except that 200 parts by mass of a terpene resin that was a tackifier resin were contained. As for this patch for treatment of eyelid diseases, the results of the measurements and evaluations of the characteristics, and the composition of the pressure-sensitive adhesive layer are shown in Table 1.

Example 7

A patch for treatment of eyelid diseases was produced in the same manner as in Example 3 except that the terpene resin that was a tackifier resin was changed to a rosin resin (KE-311 manufactured by Arakawa Chemical Industries, Ltd.). As for this patch for treatment of eyelid diseases, the results of the measurements and evaluations of the characteristics, and the composition of the pressure-sensitive adhesive layer are shown in Table 1.

Comparative Example 1

A patch for treatment of eyelid diseases was produced in the same manner as in Example 1 except that 150 parts by mass of liquid paraffin that was a softening agent were contained. As for this patch for treatment of eyelid diseases, the results of the measurements and evaluations of the characteristics, and the composition of the pressure-sensitive adhesive layer are shown in Table 1.

Comparative Example 2

A patch for treatment of eyelid diseases was produced in the same manner as in Example 1 except that 817 parts by mass of liquid paraffin that was a softening agent were contained. As for this patch for treatment of eyelid diseases, the results of the measurements and evaluations of the characteristics, and the composition of the pressure-sensitive adhesive layer are shown in Table 1.

Comparative Example 3

A patch for treatment of eyelid diseases was produced in the same manner as in Example 3 except that 150 parts by mass of a terpene resin that was a tackifier resin were contained. As for this patch for treatment of eyelid diseases, the results of the measurements and evaluations of the characteristics, and the composition of the pressure-sensitive adhesive layer are shown in Table 1.

Comparative Example 4

A patch for treatment of eyelid diseases was produced in the same manner as in Example 2 except that the support was changed to a polyethylene terephthalate film with a thickness of 25 μm [LUMIRROR (registered trademark) S-10 manufactured by Toray Industries Inc., and the Young's modulus of 4.7 GPa]. As for this patch for treatment of eyelid diseases, the results of the measurements and evaluations of the characteristics, and the composition of the pressure-sensitive adhesive layer are shown in Table 1.

Comparative Example 5

By mixing a silicone-based pressure-sensitive adhesive (BIO-PSA4501 manufactured by Dow Corning Corporation, hereinafter, may be referred to as "Si-1"), and clobetasol propionate at a proportion amount in which the content of clobetasol propionate in a pressure-sensitive adhesive layer was 0.7% by mass, and the mixture was dissolved in an ethyl acetate solution, and thus a coating fluid was prepared to form a pressure-sensitive adhesive layer with a solid content of 50% by mass. The coating fluid was applied on one surface of the release paper (a polyethylene terephthalate film subjected to a fluoridization, the thickness of 75 μm) that forms a release layer so as to give a coat thickness of 20 μm after drying, by using a bar coater, then the surface was dried, and thus a laminated body composed of the release layer and the pressure-sensitive adhesive layer (99.3% by mass of Si-1, and 0.7% by mass of clobetasol propionate were contained) was obtained. Subsequently, a patch for treatment of eyelid diseases with a thickness of 130 μm, in which on a upper surface of the pressure-sensitive adhesive layer, as a support, a low density polyethylene film (the Young's modulus of 0.12 GPa) with a thickness of 35 μm was carried and laminated, and then the support, the pressure-sensitive adhesive layer, and the release layer were provided in this order, was produced. As for this patch for treatment of eyelid diseases, the results of the measurements and evaluations of the characteristics, and the composition of the pressure-sensitive adhesive layer are shown in Table 1.

Comparative Example 6

A patch for treatment of eyelid diseases (the pressure-sensitive adhesive layer contained 99.3% by mass of Si-2 and 0.7% by mass of clobetasol propionate) was produced in the same manner as in Comparative Example 5 except that the silicone-based pressure-sensitive adhesive (Si-1) was changed to a silicone-based pressure-sensitive adhesive (BIO-PSA4102 manufactured by Dow Corning Corporation, hereinafter, may be referred to as "Si-2"). As for this patch for treatment of eyelid diseases, the results of the measurements and evaluations of the characteristics, and the composition of the pressure-sensitive adhesive layer are shown in Table 1.

TABLE 1

| Exams./ Comp. Exams. | Support | Composition of pressure-sensitive adhesive layer (parts by mass) | | | Composition of pressure-sensitive adhesive layer (% by mass) | | | |
|---|---|---|---|---|---|---|---|---|
| | | SIS | Tackifier resin | Softening agent | SIS | Tackifier resin | Softening agent | Clobetasol |
| Ex. 1 | Polyethylene (with a thickness of 35 μm) | 100 | 250 | 350 | 14.2 | 35.5 | 49.7 | 0.7 |
| Ex. 2 | Polyethylene (with a thickness of 35 μm) | 100 | 250 | 300 | 15.3 | 38.2 | 45.8 | 0.7 |
| Ex. 3 | Polyethylene (with a thickness of 35 μm | 100 | 250 | 250 | 16.6 | 41.4 | 41.4 | 0.7 |
| Ex. 4 | Polyethylene (with a thickness of 15 μm) | 100 | 250 | 300 | 15.3 | 38.2 | 45.8 | 0.7 |
| Ex. 5 | Polyethylene (with a thickness of 35 μm) | 100 (with a styrene content of 14% by mass) | 250 | 300 | 15.3 | 38.2 | 45.8 | 0.7 |
| Ex. 6 | Polyethylene (with a thickness of 35 μm) | 100 | 200 | 350 | 15.3 | 30.6 | 53.5 | 0.7 |
| Ex. 7 | Polyethylene (with a thickness of 35 μm) | 100 | 250 (Rosin resin) | 250 | 16.6 | 41.4 | 41.4 | 0.7 |

TABLE 1-continued

| | | | | | | | | |
|---|---|---|---|---|---|---|---|---|
| Comp. Ex. 1 | Polyethylene (with a thickness of 35 μm) | 100 | 250 | 150 | 19.9 | 49.7 | 29.8 | 0.7 |
| Comp. Ex. 2 | Polyethylene (with a thickness of 35 μm) | 100 | 250 | 817 | 8.5 | 21.3 | 69.5 | 0.7 |
| Comp. Ex. 3 | Polyethylene (with a thickness of 35 μm) | 100 | 150 | 250 | 19.9 | 29.8 | 49.7 | 0.7 |
| Comp. Ex. 4 | Polyethylene terephthalate (with a thickness of 25 μm) | 100 | 250 | 300 | 15.3 | 38.2 | 45.8 | 0.7 |
| Comp. Ex. 5 | Polyethylene (with a thickness of 35 μm) | | | | | (Si-1: 99.3) | | 0.7 |
| Comp. Ex. 6 | Polyethylene (with a thickness of 35 μm) | | | | | (Si-2: 99.3) | | 0.7 |

| Exams./ Comp. Exams. | Adhesivness | Flexibility | Pain at the time of removing | Residual adhesive after the removing | Adhesive force against a BA-SUS plate (N/15 mm) | Probe tack (N/5 mmφ) | Area of removed corneocyte (%) |
|---|---|---|---|---|---|---|---|
| Ex. 1 | A | AA | A | AA | 0.7 | 2.0 | 12 |
| Ex. 2 | AA | AA | A | AA | 2.0 | 2.5 | 21 |
| Ex. 3 | AA | AA | A | AA | 2.4 | 2.8 | — |
| Ex. 4 | AA | AA | AA | A | 2.0 | 2.5 | 8 |
| Ex. 5 | AA | AA | AA | A | 2.5 | 3.8 | 23 |
| Ex. 6 | AA | AA | A | AA | 0.6 | 1.8 | 23 |
| Ex. 7 | AA | AA | A | A | 1.2 | 4.5 | 16 |
| Comp. Ex. 1 | A | AA | B | AA | 5.6 | 4.4 | — |
| Comp. Ex. 2 | B | AA | AA | B | — | — | — |
| Comp. Ex. 3 | B | AA | AA | AA | 0.4 | 1.9 | — |
| Comp. Ex. 4 | B | B | AA | AA | — | — | — |
| Comp. Ex. 5 | AA | AA | B | A | — | — | 83 |
| Comp. Ex. 6 | B | AA | AA | A | 1.0 | 0.1 | — |

From Table 1, it was found that the patch for treatment of eyelid diseases in Examples 1 to 7, which is a patch for treatment of eyelid diseases that is provided with a support, a pressure-sensitive adhesive layer, and a release layer in this order,
(a) the pressure-sensitive adhesive layer includes the following (a-1) to (a-4):
(a-1) a styrene-isoprene-styrene block copolymer, a tackifier resin, and a softening agent are contained;
(a-2) a ratio (mass ratio) of the styrene-isoprene-styrene block copolymer and the tackifier resin is 1:2 to 1:4;
(a-3) a content of the softening agent is 40% to 60% by mass; and
(a-4) further 0.005% to 5% by mass of clobetasol or acid ester thereof is contained; and
(b) the support has elastic modulus with a Young's modulus of 0.01 to 0.5 GPa; had excellent adhesiveness and flexibility to the skin of eyelid, less pain at the time of removing, and less residual adhesive after the removing. Further, it was found that the patch for treatment of eyelid diseases had an adhesive force against a BA-SUS plate of 0.6 to 2.5 N/15 mm, a probe tack of 1.8 to 4.5 N/5 mmφ, and an appropriate tackiness, and further excellent characteristics in which the corneocytes removed area was 8% to 23% and thus the detachability was less, therefore, the patch for treatment of eyelid diseases that could be applied over a long period of time on the skin of eyelid where sebum was secreted, and had less residual adhesive and was gentle to the skin, was provided.

In particular, it was found that the patch for treatment of eyelid diseases in Examples 1 to 3, in which the pressure-sensitive adhesive layer was composed of a styrene-isoprene-styrene block copolymer that had a styrene content of 22% by mass and a diblock content of 15% by mass, was a patch for treatment of eyelid diseases that was furthermore excellent in the point that the residual adhesive was extremely less. It was also found that the patch for treatment of eyelid diseases in Example 4, in which the styrene-isoprene-styrene block copolymer was contained and further the support was a low density polyethylene film with a thickness of 15 μm, was a patch for treatment of eyelid diseases that was furthermore excellent in the point that the pain at the time of removing was less and the area of removed corneocyte was less as compared with the patch for treatment of eyelid diseases in Example 2, in which the pressure-sensitive adhesive layer had the same composition as that of the pressure-sensitive adhesive layer in Example 4. Further, it was found that the patch for treatment of eyelid diseases in Example 1, in which a ratio of the styrene-isoprene-styrene block copolymer and the tackifier resin was 1:2.5, was a patch for treatment of eyelid diseases that was particularly excellent in the point that the area of removed corneocytes was 12% and this was extremely less as compared with that of the patch for treatment of eyelid diseases in Example 6, in which the ratio was 1:2. Furthermore, it was also found that when the patch for treatment of eyelid diseases in Example 3 was compared to the patch for treatment of eyelid diseases in Example 7, the patch for treatment of eyelid diseases in Example 3, in which a terpene resin was contained as a tackifier resin, had a pressure-sensitive adhesive with a high cohesive force, and therefore the residual adhesive is less after removing.

In contrast, it was found that the patch for treatment of eyelid diseases in Comparative Example 1, in which the content of the softening agent in a pressure-sensitive adhesive layer was as less as around 30% by mass, caused a pain at the time of removing, and the adhesive force against a BA-SUS plate was too high, and thus the skin stimulation was large. It was also found that the patch for treatment of eyelid diseases in Comparative Example 2, in which the content of the softening agent in a pressure-sensitive adhesive layer was as much as around 70% by mass, had poor adhesiveness to the eyelid, and thus the patch might be unable to be applied for a long period of time on the skin of eyelid where sebum was secreted. Further, it was found that the patch for treatment of eyelid diseases in Comparative Example 3, in which the pressure-sensitive adhesive layer had a ratio (mass ratio) of the styrene-isoprene-styrene block copolymer and the tackifier resin of 1:1.5, had small adhesive force against a BA-SUS plate, and poor adhesiveness to the eyelid, and thus the adhesive force was insufficient, and the patch might be unable to be applied for a long period of time on the skin of eyelid where sebum was secreted. Furthermore, it was found that the patch for treatment of eyelid diseases in Comparative Example 4, in which the support was a polyethylene terephthalate film with a Young's modulus of 4.7 Gpa, had poor adhesiveness to the eyelid, and thus the patch might be unable to be applied for a long period of time on the skin of eyelid where sebum was secreted. Still furthermore, as the pressure-sensitive adhesive contained in the pressure-sensitive adhesive layer, in the case of using a silicone-based pressure-sensitive adhesive, when the silicone-based pressure-sensitive adhesive of Comparative Example 5 was contained, the amount of the corneocytes detachment was large, when the silicone-based pressure-sensitive adhesive of Comparative Example 6 was contained, the sufficient adhesiveness could not be obtained, it was inferred that the improvement of both the adhesiveness and the amount of the corneocytes detachment was difficult.

[Percutaneous Permeation Test of Clobetasol or Acid Ester Thereof]

Example 8

As for a patch for treatment of eyelid diseases that was produced in the same manner as in Example 1 except that the patch for treatment of eyelid diseases was prepared such that the content of the clobetasol propionate that was contained in a pressure-sensitive adhesive layer was 0.5% by mass, the penetrated amount of clobetasol propionate into the skin was measured. The results of the accumulated amounts ($\mu g/cm^2$) of clobetasol propionate in 6, 12, and 24 hours, which were measured for the patch for treatment of eyelid diseases, are shown in Table 2.

Comparative Example 7

As for a patch for treatment of eyelid diseases (hereinafter, may be referred to as "acrylic patch for treatment of eyelid diseases") that was produced in the same manner as in Comparative Example 5 except that the silicone-based pressure-sensitive adhesive that was contained in a pressure-sensitive adhesive layer was changed to alkyl(meth)acrylate-vinyl acetate copolymer [DURO-TAK (registered trademark) 87-4098 manufactured by Henkel Corporation] that was a solution-based acrylic polymer, that the patch for treatment of eyelid diseases was prepared such that the content of the clobetasol propionate that was contained in a pressure-sensitive adhesive layer was 0.5% by mass, and that the release paper to be used was changed to a siliconized polyethylene terephthalate, the penetrated amount of clobetasol propionate into the skin was measured. The results of the accumulated amounts ($\mu g/cm^2$) of clobetasol propionate in 6, 12, and 24 hours, which were measured for the patch for treatment of eyelid diseases, are shown in Table 2.

TABLE 2

| Example/ Comp. Exam. | Patch for treatment of eyelid diseases | Accumulated amount penetrated into the skin in 6 hours ($\mu g/cm^2$) | Accumulated amount penetrated into the skin in 12 hours ($\mu g/cm^2$) | Accumulated amount penetrated into the skin in 24 hours ($\mu g/cm^2$) |
|---|---|---|---|---|
| Example 8 | Patch for treatment of eyelid diseases according to the present invention | 0.20 | 0.58 | 1.56 |
| Comp. Exam. 7 | Acrylic patch for treatment of eyelid diseases | 0.00 | 0.04 | 0.14 |

From Table 2, as shown in the comparison of the results of Example 8 in which the patch for treatment of eyelid diseases according to the present invention, in which the pressure-sensitive adhesive layer contained a styrene-isoprene-styrene block copolymer, a tackifier resin, and a softening agent, was used, and the results of Comparative Example 7 in which the acrylic patch for treatment of eyelid diseases, in which the pressure-sensitive adhesive layer contained an acrylic system polymer, was used, as for the patch for treatment of eyelid diseases according to the present invention, it was confirmed that the percutaneous permeability of clobetasol or the acid ester thereof was extremely excellent, and thus it was found that the patch for treatment of eyelid diseases according to the present invention had sufficient percutaneous permeability even the clobetasol that was contained in the pressure-sensitive adhesive layer of the patch for treatment of eyelid diseases was low concentration.

INDUSTRIAL APPLICABILITY

The present invention is a patch for treatment of eyelid diseases that is provided with a support, a pressure-sensitive adhesive layer, and a release layer in this order, wherein (a) the pressure-sensitive adhesive layer includes the following (a-1) to (a-4):

(a-1) a styrene-isoprene-styrene block copolymer, a tackifier resin, and a softening agent are contained;

(a-2) a ratio (mass ratio) of the styrene-isoprene-styrene block copolymer and the tackifier resin is 1:2 to 1:4;

(a-3) a content of the softening agent is 40% to 60% by mass; and (a-4) further 0.005% to 5% by mass of clobetasol or acid ester thereof is contained; and (b) the support has elastic modulus with a Young's modulus of 0.01 to 0.5 GPa, therefore, a patch for treatment of eyelid diseases, which can be applied over a long period of time on the skin of eyelid where sebum is secreted, and has less residual adhesive, is gentle to the skin, and has excellent drug permeability at a low concentration, is provided, and thus the industrial applicability is high.

The invention claimed is:

1. A patch for treatment of eyelid diseases, comprising a support, a pressure-sensitive adhesive layer, and a release layer in this order, wherein
   (a-1) the pressure-sensitive adhesive layer includes a styrene-isoprene-styrene block copolymer, a tackifier resin, and a softening agent;
   (a-2) a mass ratio of the styrene-isoprene-styrene block copolymer and the tackifier resin in the pressure-sensitive adhesive layer is 1:2 to 1:4;

(a-3) a content of the softening agent in the pressure-sensitive adhesive layer is 40% to 60% by mass; and (a-4) the pressure-sensitive adhesive layer further comprises 0.005% to 5% by mass of clobetasol or acid ester thereof;

(b) the support has elastic modulus with a Young's modulus of 0.01 to 0.5 GPa;

(c) the styrene-isoprene-styrene block copolymer has a styrene content of 15% or more by mass and a diblock content of 30% or less by mass; and (d) the support is a polyethylene film with a thickness of 1 to 80 μm.

2. The patch for treatment of eyelid diseases according to claim 1, wherein
the mass ratio of the styrene-isoprene-styrene block copolymer and the tackifier resin is 1:2.4 to 1:3.5; and
the content of the softening agent is 40% to 55% by mass.

3. The patch for treatment of eyelid diseases according to claim 1, wherein
the tackifier resin is a terpene resin.

4. The patch for treatment of eyelid diseases according to claim 1, wherein
the softening agent is liquid at room temperature.

5. The patch for treatment of eyelid diseases according to claim 1, wherein
the softening agent is liquid paraffin.

6. The patch for treatment of eyelid diseases according to claim 1, wherein
a carrier film is provided on a surface of the opposite side of the pressure-sensitive adhesive layer side of the support.

7. The patch for treatment of eyelid diseases according to claim 6, wherein
the carrier film is a polyester film.

8. The patch for treatment of eyelid diseases according to claim 6, wherein
a surface of the support side of the carrier film is matt finished.

9. The patch for treatment of eyelid diseases according to claim 1, wherein
an applying area per sheet is 0.5 to 10 $cm^2$.

10. The patch for treatment of eyelid diseases according to claim 1, wherein
the patch has a shape of a rectangle, an ellipse, a crescent, a circle, a horseshoe, or a ring.

11. The patch for treatment of eyelid diseases according to claim 1, wherein
the patch provides an accumulated amount penetrated into the skin of clobetasol or acid ester thereof of 1.0 to 3.0 μg/$cm^2$ in 24 hours in an in vitro percutaneous permeability test using a hairless mouse skin.

12. A method for producing the patch for treatment of eyelid diseases according to claim 1, comprising:
forming a pressure-sensitive adhesive layer on an upper surface of a release layer.

13. The patch for treatment of eyelid diseases according to claim 7, wherein
a surface of the support side of the carrier film is matt finished.

* * * * *